US00PP33054P2

(12) United States Plant Patent
Ammerlaan

(10) Patent No.: US PP33,054 P2
(45) Date of Patent: May 11, 2021

(54) ***GASTERALOE* PLANT NAMED 'OVROCKS07'**

(50) Latin Name: *Gasteraloe beguinii*
Varietal Denomination: OVROCKS07

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 16/899,861

(22) Filed: Jun. 12, 2020

(30) Foreign Application Priority Data

Nov. 27, 2019 (QZ) ..... PBR 2019/3114

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12; A01H 5/00
See application file for complete search history.

*Primary Examiner* — Kent L Bell
(74) *Attorney, Agent, or Firm* — Samuel R. McCoy, Jr.

(57) ABSTRACT

A new and distinct variety of *Gasteraloe* plant named 'OVROCKS07' which is characterized by dark green foliage with a soft mucronate tip that is strongly suffused with a dark greyed-orange coloration, foliage which is densely covered with very light green protuberances on both the adaxial and abaxial surfaces, foliar protuberances that are arranged in irregular yet distinct longitudinal lines along the midrib and margins and otherwise randomly arranged on the leaf surface, and finely dentate foliar margins with light green teeth that are lightly suffused with greyed-orange. The new variety has shown to be uniform and stable in the resulting generations from asexual propagation.

4 Drawing Sheets

Latin name of the genus and species: The Latin name of the genus and species of the novel variety disclosed herein is *Gasteraloe beguinii*.

Variety denomination: The inventive variety of *Gasteraloe* disclosed herein has been given the variety denomination 'OVROCKS07'.

CROSS REFERENCE TO RELATED APPLICATIONS

This application claims priority to the Community Plant Variety Rights application number 2019/3114, filed on Nov. 27, 2019, which is herein incorporated by reference.

BACKGROUND OF THE INVENTION

Parentage: 'OVROCKS07' originated as a naturally occurring, whole-plant mutation of an unnamed *Gasteraloe beguinii* plant (not patented). The inventor of 'OVROCK07' is a commercial ornamental plant producer and regularly discovers mutations of *Gasteraloe* at his greenhouse operation in Bleiswijk, The Netherlands. For said mutations which seem to exhibit commercial potential, cuttings are taken to produce trial plants which are subsequently grown for evaluation.

The variety now called 'OVROCKS07' was initially discovered in the summer of 2016 as a whole-plant mutation of an unnamed *Gasteraloe* plant which exhibited lighter green foliage with uniquely arranged foliar protuberances. At the time of discovery, cuttings were taken and the resulting plants were evaluated at the inventor's greenhouse. After further evaluation it was determined that the candidate plant's unique foliage characteristics would prove favorable for commercial marketability. The new variety was given the breeder denomination 'OVROCKS07'.

Asexual Reproduction: The variety now called 'OVROCKS07' was first asexually propagated by stem cuttings in the summer of 2016 at a greenhouse in Bleiswijk, The Netherlands and has since been vegetatively propagated through four additional generations. Through subsequent generations, the unique features of this cultivar are stable and reproduced true to type.

SUMMARY OF THE INVENTION

The cultivar 'OVROCKS07' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS07'. These characteristics in combination distinguish 'OVROCKS07' as a new and distinct *Gasteraloe* cultivar:

1. 'OVROCKS07' exhibits ovate to narrowly deltoid foliage spirally arranged in a basal rosette; and
2. 'OVROCKS07' exhibits dark green foliage with a soft mucronate tip that is strongly suffused with a dark greyed-orange coloration; and
3. 'OVROCKS07' exhibits foliage which is densely covered with very light green foliar protuberances on both the adaxial and abaxial surfaces, arranged in irregular yet distinct longitudinal lines along the midrib and margins and otherwise randomly arranged on the leaf surface.

4. 'OVROCKS07' exhibits finely dentate margins with light green teeth which are lightly suffused with greyed-orange.

BOTANICAL DESCRIPTION OF THE PLANT

Figure 1:
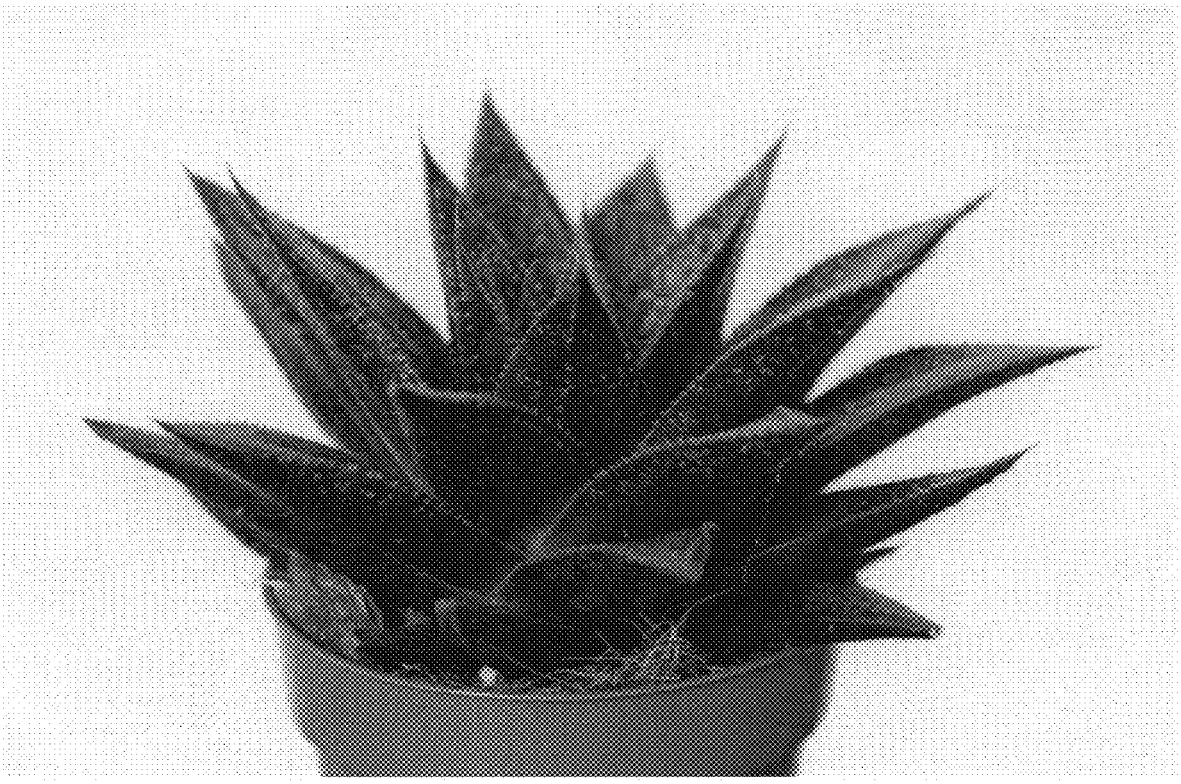
FIG. 1 illustrates, as nearly true as it is reasonably possible to make the same in color photographs of this type, an exemplary plant of 'OVROCKS07' grown in a commercial greenhouse in Bleiswijk, the Netherlands. This plant is approximately 1 year old, shown planted in a 12 cm container.
Figure 2:
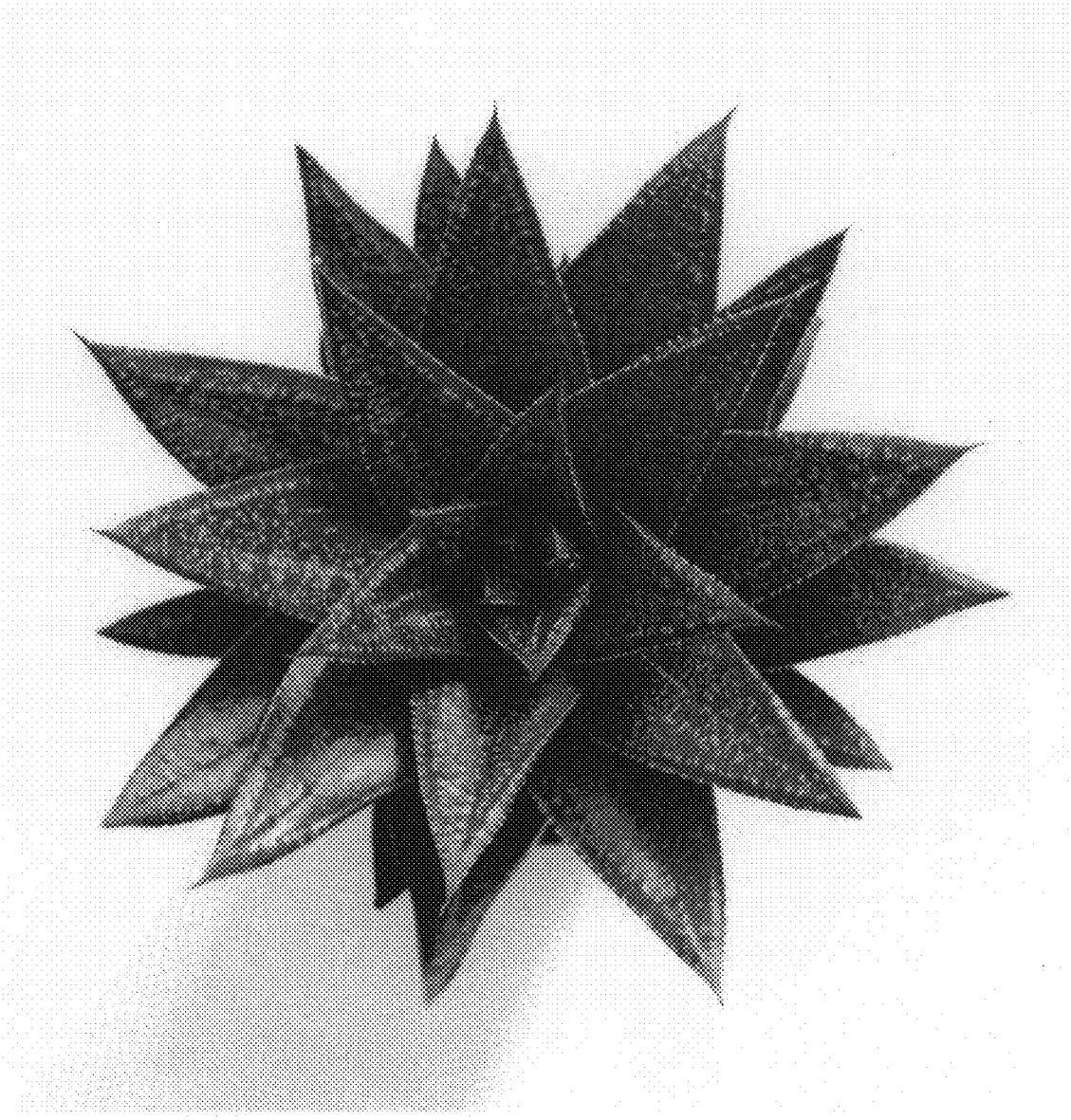
FIG. 2 illustrates, as nearly true as it is reasonably possible to make the same in color photographs of this type, the typical foliage arrangement of 'OVROCKS07'.
Figure 3:
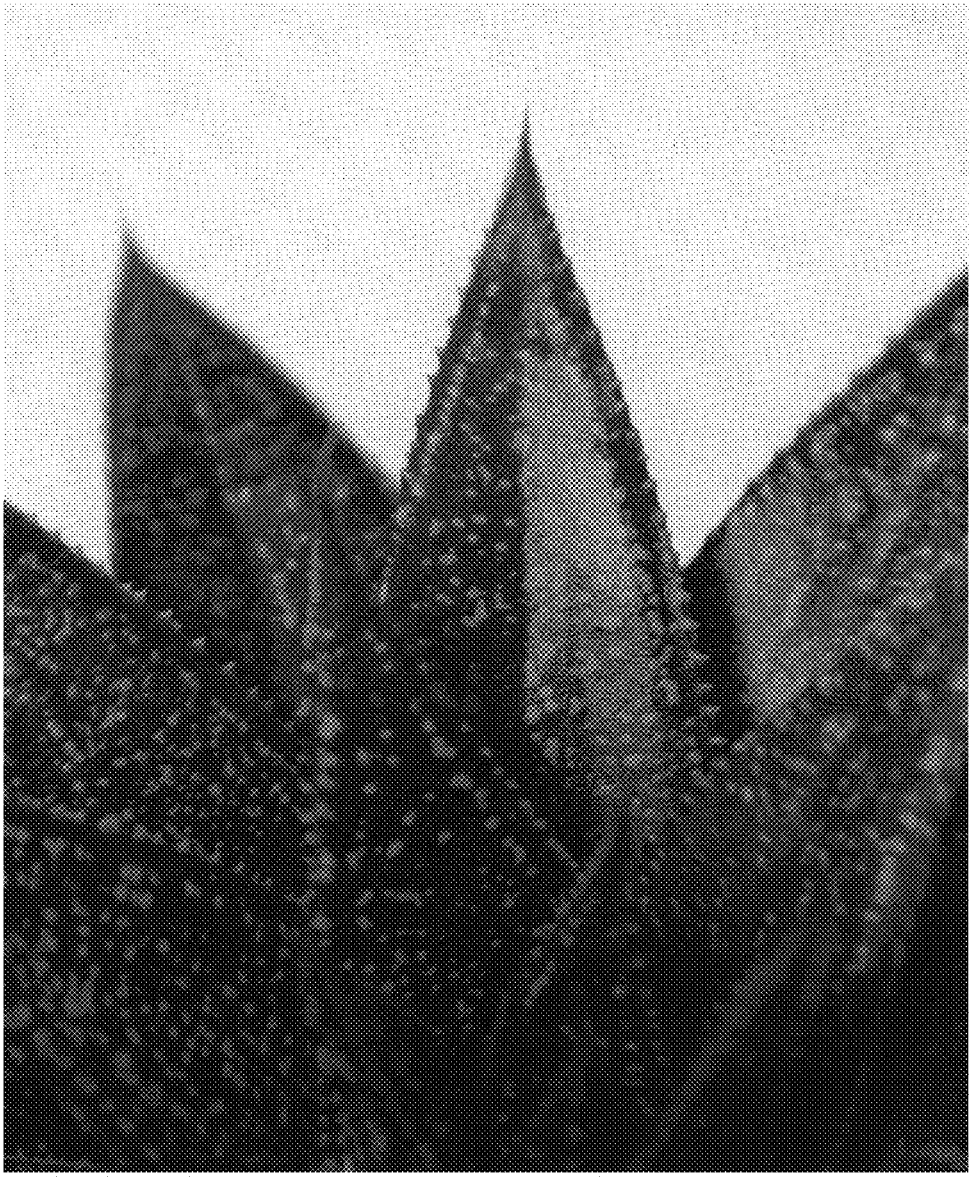
FIG. 3 illustrates, as nearly true as it is reasonably possible to make the same in color photographs of this type, the adaxial surface of the mature foliage 'OVROCKS07'.
Figure 4:
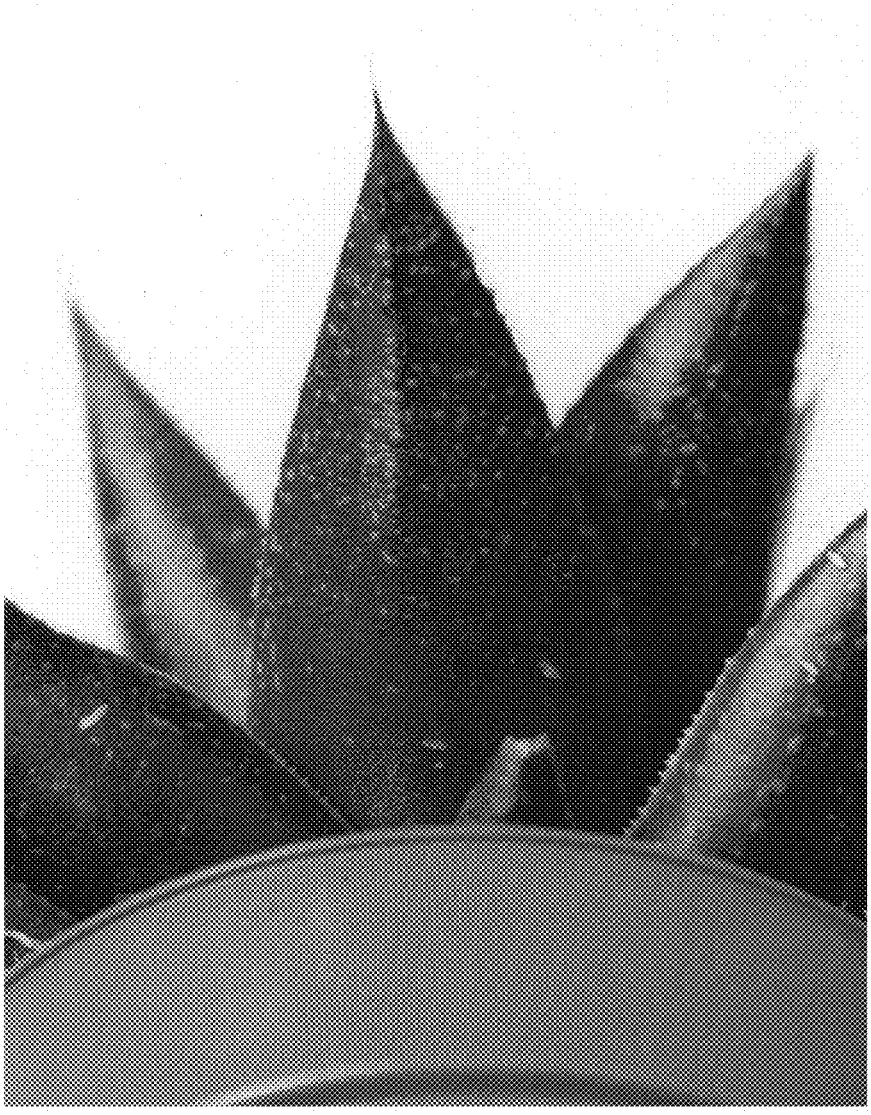
FIG. 4 illustrates, as nearly true as it is reasonably possible to make the same in color photographs of this type, the abaxial surface of the mature foliage 'OVROCKS07'.

The following observations and measurements made in November of 2019 describe averages from a sample set of six specimens of 1 year old 'OVROCKS07' plants grown in 8.5 cm nursery containers at a commercial greenhouse in Bleiswijk, the Netherlands. Plants were produced using conventional greenhouse production protocols for *Gasteraloe* which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS07' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVROCKS07' and a comparison with the parent and closest known comparator is provided below.

Plant description:

*Growth habit*.—Succulent perennial with foliage growing in a compact, non-branched basal rosette.

*Plant form*.—Flattened globular.

*Height from soil level to top of foliar plane*.—7.8 cm.

*Plant spread*.—Average of 14.1 cm.

*Growth rate*.—Moderately fast.

*Plant vigor*.—Moderately vigorous.

*Propagation*.—Type — Leaf cuttings. Time to initiate rooting — Approximately 5 weeks at an approximate temperature of 21 degrees Celsius. Crop time — Approximately 1 year to produce a marketable plant in a 7 cm container.

*Disease and pest resistance or susceptibility*.—Neither resistance nor susceptibility to typical *Gasteraloe* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Spirally arranged in a basal rosette.

*Division*.—Simple.

*Attachment*.—Sessile.

*Quantity*.—Approximately 40 leaves per rosette.

*Shape*.—Ovate to narrowly deltoid.

*Dimensions*.—8.0 cm long, 3.2 cm wide, and 0.9 cm thick.

*Aspect*.—Flat to very slightly concave.

*Attitude*.—Foliage is held more upright at and near the center of the rosette and becomes progressively more relaxed towards the outer whorls of foliage, to an average angle of 35 degrees from horizontal.

*Apex*.—Apiculate with a soft mucronate tip.

*Base*.—Broad cuneate.

*Margin*.—Finely dentate; teeth have an average length of 0.2 cm and are colored green-white, nearest to RHS 157A, with the exception of the abaxial surface of the juvenile teeth which are colored Greyed-green, nearest to RHS 191C; all marginal teeth are lightly suffused with greyed-orange, nearest to RHS N170D. Margins are not undulated or lobed.

*Pubescence and texture of the adaxial surface*.—Glabrous, smooth, and densely covered with small, round protuberances that are arranged in irregular yet distinct longitudinal lines along the midrib and margins and otherwise randomly arranged on the leaf surface; protuberance along the midrib and margins are approximately 0.03 cm tall and 0.03 cm in diameter; other protuberances are approximately 0.075 cm tall and 0.075 cm in diameter.

*Pubescence and texture of the abaxial surface*.—Glabrous, smooth, and densely covered with small, round protuberances that are arranged in irregular yet distinct longitudinal lines along the midrib and margins and otherwise randomly arranged on the leaf surface; protuberance along the midrib and margins are approximately 0.03 cm tall and 0.03 cm in diameter; other protuberances are approximately 0.05 cm tall and 0.05 cm in diameter.

*Luster of the adaxial surface*.—Moderately glossy.

*Luster of the abaxial surface*.—Moderately glossy.

*Color*.—Juvenile foliage, adaxial surface — Green, nearest to in between RHS NN137A and 139A, and fading to yellow-green towards the base, nearest to RHS 152B. The mucronate tip is colored greyed-orange, nearest to RHS N170D. Protuberances are colored greyed-green, nearest to RHS 191B. Juvenile foliage, abaxial surface — Green, nearest to RHS NN137A, and fading to yellow-green towards the base, nearest to RHS 152B. The mucronate tip is colored greyed-orange, nearest to RHS N170D. Protuberances are colored greyed-green, nearest to RHS 191B. Mature foliage, adaxial surface — Green to yellow-green, nearest to in between RHS NN137A and 147A, and fading to grey at the base, nearest to RHS 201D, and lightly suffused with white, nearest to RHS N155C. The mucronate tip is colored greyed-orange, nearest to RHS N170D. Protuberances are colored greyed-green, nearest to RHS 191B. Mature foliage, abaxial surface — Green, nearest to RHS 139A, and fading lighter towards the base, nearest to RHS 143A; base is greyed-orange, nearest to RHS N170D, and lightly suffused with white, nearest to RHS N155C. The mucronate tip is colored greyed-orange, nearest to RHS N170D. Protuberances are colored greyed-green, nearest to RHS 191B.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT

Plants of the new cultivar 'OVROCKS07' differ from the seed parent, an unnamed *Gasteraloe* plant (not patented) in the following characteristics described in Table 1 below.

TABLE 1

| Characteristic | 'OVROCKS07' | The parent. |
|---|---|---|
| General coloration of the foliage. | In between green and dark yellow-green; generally appearing as lighter green by comparison to the parent. | In between green and greyed-green; generally appearing as darker green by comparison to 'OVROCKS07'. |
| Abundance of protuberances on the abaxial foliar surface. | More abundant than the parent. | Less abundant than 'OVROCKS07'. |
| Arrangement of the foliar protuberances. | Arranged in irregular yet distinct longitudinal lines along the midrib and margins and otherwise randomly arranged on the leaf surface. | Randomly arranged on the leaf surface. |
| General coloration of the foliar protuberances. | Greyed-green, appearing as very light green. | White. |

TABLE 1-continued

| Characteristic | 'OVROCKS07' | The parent. |
|---|---|---|
| Foliage margins; abundance of the marginal teeth. | More abundant than 'OVROCKS06'. | Less abundant than 'OVROCKS07'. |
| Foliage margins; color of the marginal teeth. | Green-white and lightly suffused with greyed-orange. | Green-white. |

COMPARISONS WITH THE CLOSEST KNOWN COMPARATOR

Plants of the new cultivar 'OVROCKS07' differ from the most similar variety known to the inventor, *Gasteraloe* 'OVROCKS06' (U.S. Plant Pat. No. 31,673), in the following characteristics described in Table 2 below.

TABLE 2

| Characteristic | 'OVROCKS07' | 'OVROCKS06' |
|---|---|---|
| Foliage attitude. | More relaxed than 'OVROCKS06'. | More upright than 'OVROCKS07'. |
| General coloration of the foliage. | In between green and dark yellow-green; generally appearing as lighter green by comparison to 'OVPEARLS06'. | In between green and greyed-green; generally appearing as darker green by comparison to 'OVROCKS07'. |
| Abundance of protuberances on the abaxial foliar surface. | Less abundant than 'OVROCKS06'. | More abundant than 'OVROCKS07'. |
| Arrangement of the foliar protuberances. | Arranged in irregular yet distinct longitudinal lines along the midrib and margins and otherwise randomly arranged on the leaf surface. | Randomly arranged on the leaf surface. |
| General coloration of the foliar protuberances. | Greyed-green. appearing as very light green | Between white and green-white. |

That which is claimed is:

1. A new and distinct variety of *Gasteraloe* plant named 'OVROCKS07', substantially as described and illustrated herein.

* * * * *